(12) United States Patent
Wittorff et al.

(10) Patent No.: US 9,565,867 B2
(45) Date of Patent: Feb. 14, 2017

(54) CONFECTIONERY PRODUCT COMPRISING LOW MOLECULAR WEIGHT POLYVINYL ACETATE

(75) Inventors: Helle Wittorff, Vejle Øst (DK); Kirsten Lund, Juelsminde (DK)

(73) Assignee: GUMLINK A/S (DK)

( * ) Notice: Subject to any disclaimer, the term of this patent is extended or adjusted under 35 U.S.C. 154(b) by 1649 days.

(21) Appl. No.: 11/664,984

(22) PCT Filed: Oct. 8, 2004

(86) PCT No.: PCT/DK2004/000691
§ 371 (c)(1),
(2), (4) Date: Apr. 6, 2007

(87) PCT Pub. No.: WO2006/037319
PCT Pub. Date: Apr. 13, 2006

(65) Prior Publication Data
US 2010/0159068 A1    Jun. 24, 2010

(51) Int. Cl.
| | | |
|---|---|---|
| A23G 4/20 | (2006.01) | |
| A23G 4/08 | (2006.01) | |
| A23G 3/36 | (2006.01) | |
| A23G 4/18 | (2006.01) | |
| A24B 13/00 | (2006.01) | |
| A24B 15/10 | (2006.01) | |

(52) U.S. Cl.
CPC . *A23G 4/08* (2013.01); *A23G 3/36* (2013.01); *A23G 4/18* (2013.01); *A23G 4/20* (2013.01); *A24B 13/00* (2013.01); *A24B 15/10* (2013.01)

(58) Field of Classification Search
None
See application file for complete search history.

(56) References Cited

U.S. PATENT DOCUMENTS

| | | |
|---|---|---|
| D18,300 S | 5/1888 | Chase |
| 2,700,012 A | 1/1955 | Merckel et al. |
| 2,915,024 A | 12/1959 | Kruger et al. |
| 3,470,831 A | 10/1969 | Von Drachenfels |
| 4,032,667 A | 6/1977 | Kreuter |
| 4,127,677 A | 11/1978 | Fronczkowski et al. |
| 4,238,510 A * | 12/1980 | Cherukuri et al. ........ 426/5 |
| 4,352,822 A | 10/1982 | Cherukuri et al. |
| 4,357,359 A | 11/1982 | Cloud et al. |
| 4,385,071 A | 5/1983 | Yakimischak |
| 4,450,179 A | 5/1984 | Vink et al. |
| 4,468,185 A | 8/1984 | Jansen |
| 4,486,452 A | 12/1984 | Cloud et al. |
| 4,518,615 A | 5/1985 | Cherukuri et al. |
| 4,555,407 A | 11/1985 | Kramer et al. |
| 4,721,620 A * | 1/1988 | Cherukuri et al. ........ 426/6 |
| 4,794,003 A | 12/1988 | Cherukuri et al. |
| 4,895,732 A | 1/1990 | Suwa et al. |
| 4,933,189 A | 6/1990 | Cherukuri et al. |
| 4,968,511 A | 11/1990 | D'Amelia et al. |
| 5,002,791 A | 3/1991 | Knebl |
| 5,023,093 A | 6/1991 | Cherukuri et al. |
| 5,035,905 A | 7/1991 | Knebl |
| 5,110,608 A | 5/1992 | Cherukuri et al. |
| 5,116,626 A | 5/1992 | Synosky et al. |
| 5,125,819 A | 6/1992 | Hager et al. |
| 5,279,846 A | 1/1994 | Okumura |
| 5,480,664 A | 1/1996 | Ferrerro |
| 5,601,858 A | 2/1997 | Mansukhani et al. |
| 5,741,505 A | 4/1998 | Beyer et al. |
| 6,143,345 A | 11/2000 | Gonze et al. |
| 6,251,454 B1 | 6/2001 | Layfield |
| 6,280,780 B1 * | 8/2001 | Degady et al. ........... 426/5 |
| 6,531,114 B1 * | 3/2003 | Gmunder et al. ......... 424/48 |
| 6,558,727 B2 | 5/2003 | Degady et al. |
| 6,599,542 B1 | 7/2003 | Abdel-Malik et al. |
| 6,627,233 B1 | 9/2003 | Wolf et al. |
| 6,703,000 B2 | 3/2004 | Ning et al. |
| 6,730,344 B1 | 5/2004 | Sanders et al. |
| 6,759,079 B2 | 7/2004 | Klug et al. |
| 6,805,890 B2 | 10/2004 | Wu et al. |
| 6,838,098 B2 | 1/2005 | Bunkers et al. |
| 2002/0192330 A1 | 12/2002 | Bunkers et al. |
| 2003/0082291 A1 | 5/2003 | Davila et al. |
| 2004/0013776 A1 | 1/2004 | Whitehouse et al. |
| 2004/0115305 A1 | 6/2004 | Andersch et al. |
| 2004/0142066 A1 | 7/2004 | Andersen et al. |
| 2004/0180111 A1 | 9/2004 | Andersen et al. |
| 2006/0099300 A1 | 5/2006 | Andersen et al. |

(Continued)

FOREIGN PATENT DOCUMENTS

| | | |
|---|---|---|
| EP | 0242325 A2 | 10/1987 |
| EP | 0271445 A2 | 6/1988 |

(Continued)

OTHER PUBLICATIONS

FR 2796813 (Abstract Only).
International Search Report; International Application No. PCT/DK2004/000691; Date of Completion of Search Jun. 13, 2005;Date of Mailing of ISR Apr. 7, 2005 (4 pages).
International Preliminary Report on Patentability; International Application No. PCT/DK2004/000691; International Filing Date Aug. 10, 2004; Date of Mailing Dec. 1, 2007 (5 pages).
US Code of Federal Regulations, Title 21, Sec. 182.8013-182.8997, Oct. 26, 2005, pp. 1-3.

(Continued)

*Primary Examiner* — Nikki H Dees
(74) *Attorney, Agent, or Firm* — St. Onge Steward Johnston and Reens, LLC

(57) ABSTRACT

The invention relates to a confectionery product comprising a polymer system, flavor and sweetener, at least about 70% by weight of said polymer system comprising polyvinyl acetate (PVAc) and less than 10% by weight of said polymer system comprises polymer having a molecular weight (Mw) of greater than about 50000 g/mol.

23 Claims, No Drawings

(56) References Cited

U.S. PATENT DOCUMENTS

2009/0311368 A1    12/2009    Wittorff

FOREIGN PATENT DOCUMENTS

| | | |
|---|---|---|
| EP | 0273009 A2 | 6/1988 |
| EP | 0372695 A1 | 10/1989 |
| EP | 0 727 146 | 8/1996 |
| GB | 201 8668 | 10/1979 |
| JP | 26005888 B | 9/1951 |
| JP | 4823974 A | 3/1973 |
| JP | 56078560 A | 6/1981 |
| JP | S5712958 A | 1/1982 |
| JP | S57198050 A | 12/1982 |
| JP | 60083539 A | 5/1985 |
| JP | 62236447 A | 10/1987 |
| JP | 63214147 A | 9/1988 |
| JP | 63245638 A | 10/1988 |
| JP | 2222650 A | 9/1990 |
| JP | 10512747 T | 12/1998 |
| JP | 2000505656 A | 5/2000 |
| JP | 2002538761 A | 11/2002 |
| JP | 2004518447 T | 6/2004 |
| RU | 2176885 | 12/2001 |
| WO | WO 96/20609 | 7/1996 |
| WO | WO 00/02460 | 1/2000 |
| WO | WO 00/25598 | 5/2000 |
| WO | WO 00/40101 | 7/2000 |
| WO | WO 01/10238 | 2/2001 |
| WO | WO 01/56397 | 8/2001 |
| WO | WO 02/15708 | 2/2002 |
| WO | WO 02/19835 | 3/2002 |
| WO | 02076230 A1 | 10/2002 |
| WO | WO 02/076231 A1 | 10/2002 |
| WO | WO 03/059079 | 7/2003 |
| WO | WO 03/105594 | 12/2003 |
| WO | 2004004478 A1 | 1/2004 |
| WO | 2004004480 A1 | 1/2004 |
| WO | WO 2004/004480 A1 | 1/2004 |
| WO | 2004028265 A1 | 4/2004 |
| WO | WO 2004/028267 A1 | 4/2004 |
| WO | 2004082392 A2 | 9/2004 |
| WO | WO 2005/016021 | 2/2005 |
| WO | WO 2006/079338 | 8/2006 |

OTHER PUBLICATIONS

Food and Drug Administration, CFR, Title 21, Sec. 172,615, Masticatory Substances of Natural Vegetable Origin and Masticatory Substances, Synthetic, Apr. 1, 2001, pp. 62-63.
Manly, R.S. et al., Substances Capable of Decreasing the Acid Solubility of Tooth Enamel, J. Den. Res., vol. 28, No. 2, (1949), pp. 160-171.
Candy Formulations, with translation, Moscow, (1970), pp. 1-4.
Official Action, with translation, Application No. 1007117135, (Oct. 8, 2004), pp. 1-5.
Reynolds, James E.F., Martindale, The Extra Pharmacopoeia, 28th Ed., (1982) London, pp. 557-578.
Beckett, S.T., "Industrial Chocolate Manufacture and Use", $3^{rd}$ Ed., Blackwell Publishing Ltd. (1999).
Beckett, S.T., "The Science of Chocolate", Royal Society of Chemistry (2000).
Fiedler, H.P., Lexikon der Hilfstoffe für Pharmacie, Kosmetik und Angrenzende Gebiete (1981) pp. 63-64.
Fryer, P. et al., The Materials Science of Chocolate, MRS Bulletin (Dec. 2000).
Hunter, B,H. et al., Calcium Channel Blockers 1: a review of their mechanisms of action, Pharmacy International (Nov. 1985) pp. 267-271.
International Search Report dated Sep. 19, 2005 for Application No. PCT/DK2005/000335.
Minifie, B.W., "Chocolate, Cocoa and Confectionery", Third Ed., Van Nostrand Reinhold (1989).
Odian, G. Principles of Polymerization, Third Ed., John Wiley & Sons, Inc. New York, (1991) p. 17.
Opinion dated Jun. 30, 2005 for Application No. PCT/DK2004/000691.
Opinion dated Sep. 15, 2005 for Application No. PCT/DK2005/000335.
Notification for Application No. PCT/DK2005/000335.
Preliminary Patentability Report dated Apr. 11, 2007 for Application No. PCT/DK2005/000335.
Search Report dated Apr. 13, 2006 for Application No. PCT/DK2004/000691.
Japanese Office Action; Application No. 2007-535017; Mailed from JPO on Dec. 27, 2010; 6 pages.
NPL PVAc and Tg Retrieved Jul. 19, 2013. The Webpage updated Jul. 11, 2000.

* cited by examiner

CONFECTIONERY PRODUCT COMPRISING LOW MOLECULAR WEIGHT POLYVINYL ACETATE

FIELD OF THE INVENTION

The invention relates to a confectionery product comprising a polymer system, flavor and sweetener.

BACKGROUND OF THE INVENTION

Vast numbers of variations of chewing gum are disclosed in the prior art. The chewing gum is typically characterized as a polymer based article having a gum featuring elastomeric properties. These elastomeric properties are maintained by careful dimensioning of the gum base in view of the applied chewing ingredients for the purpose of obtaining the desired chewing gum characteristic.

It is the object of the invention to provide a confectionery product having toffee-like textural properties.

SUMMARY OF THE INVENTION

The invention relates to a confectionery product comprising a polymer system, flavor and sweetener, at least about 70% by weight of said polymer system comprising polyvinyl acetate (PVAc) and less than 10% by weight of said polymer system comprises polymer having a molecular weight (Mw) of greater than about 50000 g/mol.

In an embodiment of the invention said confectionery product comprises a polymer system in an amount of from about 5 to about 99% by weight, flavor in an amount of about 0.001 to about 30% by weight and sweeteners in an amount of about 5% to about 80% by weight.

According to the invention, a toffee-like chewing gum has been obtained. The backbone of the product is a polymer system, basically equivalent in function to the gum base of conventional chewing gum although with significant textural differences.

Furthermore, in addition to the obtained textural properties, an improved release of chewing gum ingredients such as flavours and sweeteners (active ingredients) has been obtained.

In an embodiment of the invention said confectionery product comprises a chewable tablet comprising a chewable polymer system.

According to the invention, the confectionery product may be evaluated to have advantageous textural properties comparable to toffee. Such hybrid confectionery product may thus be dimensioned to be a hybrid toffee chewing gum product. The toffee texture of the polymer based confectionery product according to the invention is obtained through a substantial amount of polyvinyl acetate and avoiding use of substantial amounts of high molecular weight polymers, in particular elastomers.

In an embodiment of the invention the polymer system is substantially formed by polyvinyl acetate(s) alone.

Basically, a polymer system comprising solely polyvinyl acetate(s) alone is preferred in the sense that e.g. natural resins tend to counteract the—in this context—desired toffee-like properties.

In an embodiment of the invention the confectionery product comprises less than 4% by weight of filler, preferably less than 1% by weight.

According to a preferred embodiment of the invention, the amount of filler in the chewing gum or the polymer system should be kept low in order to maintain the desired toffee-like texture of the confectionery tablet.

In an embodiment of the invention the confectionery product is substantially free of filler.

According to a further preferred embodiment of the invention, fillers such as talc, should be avoided, as the desired toffee-like texture may be counteracted by the influencing of the filler on the mainly PVA-based polymer system of the tablet.

In an embodiment of the invention said polymer system comprises plasticizer(s).

According to an embodiment of the invention, plasticizers are applied for the purpose of obtaining a soft chew feel of the polyvinyl acetate based polymer system. It is noted that the desired plasticization depends heavily on the other ingredients applied in the product. As an example, some aggressive flavors, such as fruit flavors and acids, tend to soften the polymer system significantly compared to e.g. mint oil-based flavors.

Particularly useful plasticizers according to the present invention are triacetin, acetylated mono- and di- and triglycerides of short chain fatty acids, acetylated mono- and di- and triglycerides of medium chain fatty acids, acetylated monoglycerides of long chain fatty acids, methyl ester of rosin, low molecular weight PVAc.

A preferred plasticizer will in a preferred embodiment have a hydrophilicity corresponding to the applied PVAc.

In an embodiment of the invention said polymer system comprises less than 30% by weight of plasticizers, preferably less than 20% by weight of plasticizers and most preferably less than 10% by weight of plasticizers.

In an embodiment of the invention the confectionery product comprises less than 10% by weight of plasticizers, preferably less than 8% by weight of plasticizers and most preferably less than 4% by weight of plasticizers.

According to a preferred embodiment of the invention, a relatively low amount of plasticizers should be applied in order to obtain the desired textural properties, i.e. the toffee-like chew feel. Moreover, off-notes may be present if too much plasticizer is present, especially when applying triacetin and glycerides. Finally, plasticizers such as triacetin and acetylated glycerides are expensive and the amount should be kept low.

In an embodiment of the invention said plasticizer comprises triacetin.

In an embodiment of the invention said plasticizer comprises acetylated glycerides.

In an embodiment of the invention said polymer system comprises less than 4% by weight of polymers having a molecular weight (Mw) of from about 50000 to 99999 g/mol.

In an embodiment of the invention said polymer system comprises less than 2% by weight of polymers having a molecular weight (Mw) of from about 100000 to 199999 g/mol.

In an embodiment of the invention said polymer system comprises less than 1% by weight of polymers having a molecular weight (Mw) of from about 200000 to 399999 g/mol.

In an embodiment of the invention said polymer system comprises less than 0.5% by weight of polymers having a molecular weight (Mw) of from about 399000 to 800000 g/mol.

According to an embodiment of the invention high molecular weight polymers, such as conventional elastomers or high molecular weight PVAc, should be kept low in concentration to obtain the desired texture.

In an embodiment of the invention said polymer system is substantially free of elastomers.

In an embodiment of the invention said polymer system substantially comprises polyvinyl acetate (PVAc) alone.

According to a preferred embodiment of the invention, conventional elastomers should be avoided in order to avoid the typical chewing gum-like elastomeric properties. According to a most preferred embodiment of the invention, the polymers of the product consist of polyvinyl acetate.

Evidently, insignificant amounts of other polymers may be acceptable within the scope of the invention without compromising the principles of the invention, namely that the PVAc alone provide a toffee-like texture.

In an embodiment of the invention the polymer system comprises at least one low molecular weight PVA having a molecular weight (Mw) of about 2000 to 40000 g/mol,
at least one high molecular weight PVA having a molecular weight (Mw) of 40001 to 200000 g/mol.

In an embodiment of the invention the polymer system comprises
at least one low molecular weight (Mw) PVA having a molecular weight of about 9000 to 30000 g/mol, preferably about 13 000 to 21000 g/mol.

In an embodiment of the invention the confectionery product comprises at least one low molecular weight PVA having a molecular weight (Mw) of about 2000 to 40000 g/mol in an amount of from about 70 to 99% by weight of the polymer system In an embodiment of the invention, the confectionery product comprises at least one high molecular weight PVA having a molecular weight (Mw) of 40000 to 100000 in an amount of from about 0.5 to 10% by weight of the polymer system.

In an embodiment of the invention said flavor comprises substantially oil-based flavors.

According to an embodiment of the invention, substantially oil-based flavors are preferred as such flavors tend to match the polymer system, which according to the invention may be regarded hydrophilic.

According to a further embodiment of the invention, substantially hydrophilic flavors have proved advantageous e.g. with respect to prolongation of release.

In an embodiment of the invention said sweeteners comprises sugar.

In an embodiment of the invention said sweeteners comprises artificial sweeteners.

According to a preferred embodiment of the invention, artificial sweeteners may advantageously be applied in the toffee-gum-like confectionery product.

In an embodiment of the invention, the weight of the confectionery product is from about ¼ gram to about 10 grams, preferably from about ½ gram to about 5 grams.

In an embodiment of the invention the confectionery product comprises a coating.

The confectionery product according to the invention is suitable for almost any coating method within the art, such as hard coating, film coating, soft coating, etc.

In a further advantageous embodiment of the invention, several layers of coatings may be applied and the layers may comprise or be formed by different types of layer substance.

In an advantageous embodiment of the invention, chocolate may be applied as a coating, a product module or center filling as the polymer system has proved robust to such quite aggressive plasticizing component, which typically tends to dissolve conventional chewing gum formulations.

In accordance with the invention, the confectionery product comprises about 0 to about 75% by weight of an outer coating applied onto the confectionery product center. Suitable coating types include hard coatings, film coatings and soft coatings of any composition including those currently used in coating of chewing gum, pharmaceutical products and confectioneries.

According to a preferred embodiment of the invention, film coating is applied to the confectionery product.

One presently preferred outer coating type is a hard coating, which term is used in the conventional meaning of that term including sugar coatings and sugar-free (or sugarless) coatings and combinations thereof. The object of hard coating is to obtain a sweet, crunchy layer which is appreciated by the consumer and to protect the confectionery product centers. In a typical process of providing the confectionery product centers with a protective sugar coating the confectionery product centers are successively treated in suitable coating equipment with aqueous solutions of crystallizable sugar such as sucrose or dextrose, which, depending on the stage of coating reached, may contain other functional ingredients, e.g. fillers, colors, etc. In the present context, the sugar coating may contain further functional or active compounds including flavor compounds, pharmaceutically active compounds and/or polymer degrading substances.

In the production of confectionery product it may, however, be preferred to replace the cariogenic sugar compounds in the coating by other, preferably crystallisable, sweetening compounds that do not have a cariogenic effect. In the art such coatings are generally referred to as sugarless or sugar-free coatings. Presently preferred non-cariogenic hard coating substances include polyols, e.g. sorbitol, maltitol, mannitol, xylitol, erythritol, lactitol, isomalt and tagatose which are obtained by industrial methods by hydrogenation of D-glucose, maltose, fructose or levulose, xylose, erythrose, lactose, isomaltulose and D-galactose, respectively.

In a typical hard coating process, as it will be described in details in the following, syrup containing crystallisable sugar and/or polyol is applied onto the confectionery product centers and the water it contains is evaporated off by blowing with warm, dry air. This cycle must be repeated several times, typically 10 to 80 times, in order to reach the swelling required. The term "swelling" refers to the increase in weight of the products, as considered at the end of the coating operation by comparison with the beginning, and in relation to the final weight of the coated products. In accordance with the present invention, the coating layer constitutes for example about 0 to 75% by weight of the finished confectionery product, such as about 10 to 60% by weight, including about 15 to 50% by weight.

In further useful embodiments the outer coating of the confectionery product element of the invention is an element that is subjected to a film coating process and which therefore comprises one or more film-forming polymeric agents and optionally one or more auxiliary compounds, e.g. plasticizers, pigments and opacifiers. A film coating is a thin polymer-based coating applied to a confectionery product center of any of the above forms. The thickness of such a coating is usually between 20 and 100 μm. Generally, the film coating is obtained by passing the confectionery product centers through a spray zone with atomized droplets of the coating materials in a suitable aqueous or organic solvent vehicle, after which the material adhering to the confectionery product centers is dried before the next portion of coating is received. This cycle is repeated until the coating is complete.

In the present context, suitable film-coating polymers include edible cellulose derivatives such as cellulose ethers including methylcellulose (MC), hydroxyethyl cellulose (HEC), hydroxypropyl cellulose (HPC) and hydroxypropyl methylcellulose (HPMC). Other useful film-coating agents are acrylic polymers and copolymers, e.g. methylacrylate aminoester copolymer or mixtures of cellulose derivatives and acrylic polymers. A particular group of film-coating polymers also referred to as functional polymers are polymers that, in addition to its film-forming characteristics, confer a modified release performance with respect to active components of the confectionery product formulation. Such release modifying polymers include methylacrylate ester copolymers, ethylcellulose (EC) and enteric polymers designed to resist the acidic stomach environment, yet dissolve readily in the duodenum. The latter group of polymers includes: cellulose acetate phthalate (CAP), polyvinyl acetate phthalate (PVAP), shellac, metacrylic acid copolymers, cellulose acetate trimellitate (CAT) and HPMC. It will be appreciated that the outer film coating according to the present invention may comprise any combination of the above film-coating polymers.

In other embodiments, the film-coating layer of the confectionery product elements according to the invention comprises a plasticizing agent having the capacity to alter the physical properties of a polymer to render it more useful in performing its function as a film-forming material. In general, the effect of plasticizers will be to make the polymer softer and more pliable as the plasticizer molecules interpose themselves between the individual polymer strands thus breaking down polymer-polymer interactions. Most plasticizers used in film coating are either amorphous or have very little crystallinity. In the present context, suitable plasticizers include polyols such as glycerol, propylene glycol, polyethylene glycol, e.g. the 200-6000 grades hereof, organic esters such as phthalate esters, dibutyl sebacate, citrate esters and triacetin, oils/glycerides including castor oil, acetylated monoglycerides and fractionated coconut oil.

The choice of film-forming polymer(s) and plasticizing agent(s) for an optional outer coating of the present confectionery product is made with due consideration for achieving the best possible barrier properties of the coating in respect of dissolution and diffusion across the film of moisture and gasses.

The film coating of the confectionery product elements may also contain one or more colorants or opacifiers. In addition to providing a desired color, such agents may contribute to protecting the confectionery product against pre-chewing reactions, in particular by forming a barrier against moisture and gasses. Suitable colorants/pacifiers include organic dyes and their lakes, inorganic coloring agents, e.g. titanium oxide and natural colors such as e.g. β-carotene.

Additionally, film coatings may contain one or several auxiliary substances such as flavors and waxes or saccharide compounds such as polydextrose, dextrins including maltodextrin, lactose, modified starch, a protein such as gelatine or zein, a vegetable gum and any combination thereof.

It is also an aspect of the present invention that the outer coating of the confectionery product can contain one or more pharmaceutically or cosmetically components including those mentioned hereinbefore.

Accordingly, in further embodiments, an above hard-coated or film-coated confectionery product element of the invention is an element where the outer coating comprises at least one additive component selected from a binding agent, a moisture absorbing component, a film forming agent, a dispersing agent, an antisticking component, a bulking agent, a flavoring agent, a coloring agent, a pharmaceutically or cosmetically active component, a lipid component, a wax component, a sugar, and an acid. If it is desired to defer the effect of any of these additive components in the outer coating until mastication of the confectionery product, such components may, in accordance with the invention be encapsulated using any conventional encapsulation agent such as e.g. a protein including gelatine and soy protein, a cellulose derivative including any of those mentioned above, a starch derivative, edible synthetic polymers and lipid substances, the latter optionally in the form of liposome encapsulation.

In other embodiments, the confectionery product element according to the invention is provided with an outer coating in the form generally described in the art as a soft coating. Such soft coatings are applied using conventional methods and may advantageously consist of a mixture of a sugar or any of the above non-cariogenic, sugar-less sweetening compounds, and a starch hydrolysate.

Again, it should be noted that the above-described coating is optional or that it may be postponed until it fits into the last part of the manufacturing process due to the fact that the applied barrier layer is also acting as a complete or at least a partial barrier to transfer of humidity from the environment into the tablet.

In an embodiment of the invention, the confectionery product may be formed in different shapes such as cores, ellipsoid, balls, cylinders, squares, rectangular, hexagonal, strips, paraboloid, donut formed, ring formed and/or multimodular. Likewise, the product may be center filled.

In an embodiment of the invention the confectionery product comprises active ingredients.

Examples of suitable active ingredients are listed below.

In one embodiment the confectionery product according to the invention comprises a pharmaceutically, cosmetically or biologically active substance. Examples of such active substances, a comprehensive list of which is found e.g. in WO 00/25598, which is incorporated herein by reference, include drugs, dietary supplements, antiseptic agents, pH adjusting agents, anti-smoking agents and substances for the care or treatment of the oral cavity and the teeth such as hydrogen peroxide and compounds capable of releasing urea during chewing. Examples of useful active substances in the form of antiseptics include salts and derivatives of guanidine and biguanidine (for instance chlorhexidine diacetate) and the following types of substances with limited water-solubility: quaternary ammonium compounds (e.g. ceramine, chloroxylenol, crystal violet, chloramine), aldehydes (e.g. paraformaldehyde), derivatives of dequaline, polynoxyline, phenols (e.g. thymol, p-chlorophenol, cresol), hexachlorophene, salicylic anilide compounds, triclosan, halogenes (iodine, iodophores, chloroamine, dichlorocyanuric acid salts), alcohols (3,4 dichlorobenzyl alcohol, benzyl alcohol, phenoxyethanol, phenylethanol), cf. also Martindale, The Extra Pharmacopoeia, 28th edition, pages 547-578; metal salts, complexes and compounds with limited water-solubility, such as aluminum salts, (for instance aluminum potassium sulphate AlK $(SO_4)_2$, $12H_2O$) and salts, complexes and compounds of boron, barium, strontium, iron, calcium, zinc, (zinc acetate, zinc chloride, zinc gluconate), copper (copper chloride, copper sulphate), lead, silver, magnesium, sodium, potassium, lithium, molybdenum, vanadium should be included; other compositions for the care of mouth and teeth: for instance; salts, complexes and compounds containing fluorine (such as sodium fluoride, sodium monofluorophosphate, aminofluorides, stannous fluoride), phosphates, carbonates and selenium. Further active substances can be found in J. Dent. Res. Vol. 28 No. 2, pages 160-171,1949.

Examples of active substances in the form of agents adjusting the pH in the oral cavity include: acids, such as adipic acid, succinic acid, fumaric acid, or salts thereof or salts of citric acid, tartaric acid, malic acid, acetic acid, lactic acid, phosphoric acid and glutaric acid and acceptable bases, such as carbonates, hydrogen carbonates, phosphates, sulphates or oxides of sodium, potassium, ammonium, magnesium or calcium, especially magnesium and calcium.

Active ingredients may comprise the below mentioned compounds or derivates thereof but are not limited thereto: Acetaminophen, Acetylsalicylic acid, Buprenorphine, Bromhexin, Celcoxib, Codeine, Diphenhydramin, Diclofenac, Etoricoxib, Ibuprofen, Indometacin, Ketoprofen, Lumiracoxib, Morphine, Naproxen, Oxycodon, Parecoxib, Piroxicam, Pseudoefedrine, Rofecoxib, Tenoxicam, Tramadol, Valdecoxib, Calcium carbonate, Magaldrate, Disulfram, Bupropion, Nicotine, Azithromycin, Clarithromycin, Clotrimazole, Erythromycin, Tetracycline, Granisetron, Ondansetron, Prometazin, Tropisetron, Brompheniramine, Ceterizin, leco-Ceterizin, Chlorcyclizine, Chlorpheniramin, Chlorpheniramin, Difenhydramine, Doxylamine, Fenofenadin, Gualfenesin, Loratidin, des-Loratidin, Phenyltoloxamine, Promethazin, Pyridamine, Terfenadin, Troxerutin, Methyldopa, Methylphenidate, Benzalcon, Chloride, Benzeth, Chloride, Cetylpyrid, Chloride, Chlorhexidine, Ecabet-sodium, Haloperidol, Allopurinol, Colchinine, Theophylline, Propanolol, Prednisolone, Prednisone, Fluoride, Urea, Actot, Glibenclamide, Glipizide, Metformin, Miglitol, Repaglinide, Rosiglitazone, Apomorfin, Cialis, Sildenafil, Vardenafil, Diphenoxylate, Simethicone, Cimetidine, Famotidine, Ranitidine, Ratinidine, cetrizin, Loratadine, Aspirin, Benzocaine, Dextrometorphan, Phenylpropanolamine, Pseudoephedrine, Cisapride, Domperidone, Metoclopramide, Acyclovir, Dioctylsulfosucc, Phenolphtalein, Almotriptan, Eletriptan, Ergotamine, Migea, Naratriptan, Rizatriptan, Sumatriptan, Zolmitriptan, Aluminum salts, Calcium salts, Ferro salts, Ag-salts, Zinc-salts, Amphotericin B. Chlorhexidine, Miconazole, Triamcinolonacetonid, Melatonine, Phenobarbitol, Caffeine, Benzodiazepiner, Hydroxyzine, Meprobamate, Phenothiazine, Buclizine, Brometazine, Cinnarizine, Cyclizine, Difenhydramine, Dimenhydrinate, Buflomedil, Amphetamine, Ephedrine, Orlistat, Phenylephedrine, Phenylpropanolamin, Pseudoephedrine, Sibutram in, Ketoconazole, Nitroglycerin, Nystatin, Progesterone, Testosterone, Vitamin B12, Vitamin C, Vitamin A, Vitamin D, Vitamin E, Pilocarpin, Aluminumaminoacetat, Cimetidine, Esomeprazole, Famotidine, Lansoprazole, Magnesiumoxide, Nizatide and or Ratinidine.

The invention is suitable for increased or accelerated release of active agents selected among the group of dietary supplements, oral and dental compositions, antiseptic agents, pH adjusting agents, anti-smoking agents, sweeteners, flavorings, aroma agents or drugs. Some of those will be described below.

The active agents to be used in connection with the present invention may be any substance desired to be released from the confectionery product. The active agents, for which a controlled and/or accelerated rate of release is desired, are primarily substances with a limited water-solubility, typically below 10 g/100 ml inclusive of substances which are totally water-insoluble. Examples are medicines, dietary supplements, oral compositions, anti-smoking agents, highly potent sweeteners, pH adjusting agents, flavorings etc.

Other active ingredients are, for instance, paracetamol, benzocaine, cinnarizine, menthol, carvone, caffeine, chlorhexidine-di-acetate, cyclizine hydrochloride, 1,8-cineol, nandrolone, miconazole, mystatine, sodium fluoride, nicotine, cetylpyridinium chloride, other quaternary ammonium compounds, vitamin E, vitamin A, vitamin D, glibenclamide or derivatives thereof, progesterone, acetylsalicylic acid, dimenhydrinate, cyclizine, metronidazole, sodium hydrogen carbonate, the active components from ginkgo, the active components from propolis, the active components from ginseng, methadone, oil of peppermint, salicylamide, hydrocortisone or astemizole.

Examples of active agents in the form of dietary supplements are for instance salts and compounds having the nutritive effect of vitamin B2 (riboflavin), B12, folinic acid, folic acid, niacine, biotine, poorly soluble glycerophosphates, amino acids, the vitamins A, D, E and K, minerals in the form of salts, complexes and compounds containing calcium, phosphorus, magnesium, iron, zinc, copper, iodine, manganese, chromium, selenium, molybdenum, potassium, sodium or cobalt.

Furthermore, reference is made to lists of nutritionists accepted by the authorities in different countries such as for instance US code of Federal Regulations, Title 21, Section 182.5013.182 5997 and 182.8013-182.8997.

Examples of active agents in the form of compounds for the care or treatment of the oral cavity and the teeth are for instance bound hydrogen peroxide and compounds capable of releasing urea during chewing.

Examples of active agents in the form of antiseptics are for instance salts and compounds of guanidine and biguanidine (for instance chlorhexidine diacetate) and the following types of substances with limited water-solubility: quaternary ammonium compounds (for instance ceramine, chloroxylenol, crystal violet, chloramine), aldehydes (for instance paraformaldehyde), compounds of dequaline, polynoxyline, phenols (for instance thymol, para chlorophenol, cresol) hexachlorophene, salicylic anilide compounds, triclosan, halogenes (iodine, iodophores, chloroamine, dichlorocyanuric acid salts), alcohols (3,4 dichlorobenzyl alcohol, benzyl alcohol, phenoxyethanol, phenylethanol), cf. furthermore Martindale, The Extra Pharmacopoeia, 28th edition, pages 547-578; metal salts, complexes and compounds with limited water-solubility, such as aluminum salts, (for instance aluminum potassium sulphate AlK $(SO_4)_2$, $12H_2O$) and furthermore salts, complexes and compounds of boron, barium, strontium, iron, calcium, zinc, (zinc acetate, zinc chloride, zinc gluconate), copper (copper chloride, copper sulfate), lead, silver, magnesium, sodium, potassium, lithium, molybdenum, vanadium should be included; other compositions for the care of mouth and teeth: for instance; salts, complexes and compounds containing fluorine (such as sodium fluoride, sodiummono-fluorophosphate, amino fluorides, stannous fluoride), phosphates, carbonates and selenium.

Cf. furthermore J. Dent. Res. Vol. 28 No. 2, pages 160-171, 1949, wherein a wide range of tested compounds is mentioned.

Examples of active agents in the form of agents adjusting the pH in the oral cavity include for instance: acceptable acids, such as adipic acid, succinic acid, fumaric acid, or salts thereof or salts of citric acid, tartaric acid, malic acid, acetic acid, lactic acid, phosphoric acid and glutaric acid and acceptable bases, such as carbonates, hydrogen carbonates, phosphates, sulfates or oxides of sodium, potassium, ammonium, magnesium or calcium, especially magnesium and calcium.

Examples of active agents in the form of anti-smoking agents include for instance: nicotine, tobacco powder or silver salts, for instance silver acetate, silver carbonate and silver nitrate.

In a further embodiment, the sucrose fatty acid esters may also be utilized for increased release of sweeteners including for instance the so-called highly potent sweeteners, such as for instance saccharin, cyclamate, aspartame, thaumatin, dihydrocalcones, stevioside, glycyrrhizin or salts or compounds thereof. For increased released of sweetener, the sucrose fatty acids preferable have a content of palmitate of at least 40% such as at least 50%.

Further examples of active agents are medicines of any type.

Examples of active agents in the form of medicines include caffeine, salicylic acid, salicyl amide and related substances (acetylsalicylic acid, choline salicylate, magnesium salicylate, sodium salicylate), paracetamol, salts of pentazocine (pentazocine hydrochloride and pentazocine-lactate), buprenorphine hydrochloride, codeine hydrochloride and codeine phosphate, morphine and morphine salts (hydrochloride, sulfate, tartrate), methadone hydrochloride, ketobemidone and salts of ketobemidone (hydrochloride), beta-blockers, (propranolol), calcium antagonists, verapamil hydrochloride, nifedinpine as well as suitable substances and salts thereof mentioned in Pharm. Int., November 85, pages 267-271, Barney H. Hunter and Robert L. Talbert, nitroglycerine, erythrityl tetranitrate, strychnine and salts thereof, lidocaine, tetracaine hydrochloride, etorphine hydrochloride, atropine, insulin, enzymes (for instance papain, trypsin, amyloglucosidase. glucoseoxidase, streptokinase, streptodornase, dextranase, alpha amylase), polypeptides (oxytocin, gonadorelin, (LH.RH), desmopressin acetate (DDAVP), isoxsuprine hydrochloride, ergotamine compounds, chloroquine (phosphate, sulfate), isosorbide, demoxytocin, heparin.

Other active ingredients include beta-lupeol, Letigen®, Sildenafil citrate and derivatives thereof.

Dental products include Carbamide, CPP Casein Phospho Peptide; Chlorhexidine, Chlorhexidine di acetate, Chlorhexidine Chloride, Chlorhexidine di gluconate, Hexetedine, Strontium chloride, Potassium Chloride, Sodium bicarbonate, Sodium carbonate, Fluor containing ingredients, Fluorides, Sodium fluoride, Aluminum fluoride.

Ammonium fluoride, Calcium fluoride, Stannous fluoride, Other fluor containing ingredients Ammonium fluorosilicate, Potassium fluorosilicate, Sodium fluorosilicate, Ammonium monofluorphosphate, Calcium monofluorphosphate, Potassium monofluorphosphate, Sodium monofluorphosphate, Octadecentyl Ammonium fluoride, Stearyl Trihydroxyethyl Propylenediamine Dihydrofluoride, Vitamins include A, B1, B2, B6, B12, Folinic acid, Folic acid, niacin, Pantothenic acid, biotine, C, D, E, K. Minerals include Calcium, phosphorus, magnesium, iron, Zinc, Copper, Iodine, Manganese, Chromium, Selenium, Molybdenum. Other active ingredients include: Q10, enzymes. Natural drugs including Ginkgo, Biloba, ginger, and fish oil.

Moreover, the invention relates to a method of manufacturing a confectionery product, whereby the product is manufactured by a batch process.

A well-known batch manufacturing method is a two-step process according to which the polymer system (within the terms of chewing gum referred to as the gum base) is mixed in a first step on the basis of substantially hydrophobic components and in where the further hydrophilic components such as sweeteners etc. are mixed together with the polymer system.

Moreover, the invention relates to a method of manufacturing a confectionery product, whereby the product is manufactured by an extruder process.

Manufacturing of the confectionery product and/or the polymer system of the product may advantageously be performed by extruding. The process is very attractive and advantageous in relation to the present invention due to the fact that the polymer system (the gum base equivalent) comprises very few components, e.g. preferably three components: a LMw PVAc, a HMw PVAc, and a plasticizer, e.g. triacetin.

DETAILED DESCRIPTION

General description of the confectionery product composition.

In general, a confectionery product composition according to the present invention typically comprises a water-soluble bulk portion, a water-insoluble chewable polymer system portion, and flavoring agents. The water-soluble portion dissipates with a portion of the flavoring agent over a period of time during chewing. The polymer system portion is retained in the mouth throughout the chew. To a certain degree, the polymer system fully corresponds to a conventional gum base, both with respect to manufacturing, ingredients and to a certain degree release. The main difference is found in composition and textural properties of the polymer system.

General description of the polymer system composition.

The polymer system is the masticatory substance of the confectionery product according to the invention, which imparts the chew characteristics to the final product. The polymer system typically defines the release profile of flavours, and sweeteners and plays a significant role in the final product.

The insoluble portion of the confectionery product typically may contain any combination of PVAc's, plasticizers, waxes, softeners, fillers and other optional ingredients such as colorants and antioxidants. Further elastomers or high molecular weight PVAc's may be applied in the polymer system to a very limited degree without compromising the desired toffee-like texture.

The composition of the polymer system formulations can vary substantially depending on the particular product to be prepared and on the desired masticatory and other sensory characteristics of the final product.

General description of polymer system ingredients.
Function of Elastomers

The amount of elastomers and in particular high molecular weight elastomers should be kept very low or preferably be completely omitted according to the invention. According to a preferred embodiment the polymer system and the final confectionery product should be substantially free of elastomer. However, when used, e.g. for the purpose of making the polymer system robust elastomers may provide the rubbery, cohesive nature to the confectionery product which varies depending on this ingredient's chemical structure and how it may be compounded with other ingredients. Elastomers suitable for use in the polymer system of the present invention may include natural or synthetic types.

The elastomer may be any water-insoluable polymer known in the art, and includes those polymers utilized for chewing gum and bubble gum listed in Food and Drug Administration, CFR, Title 21, Section 172,615, as "Masticatory Substances of Natural Vegetable Origin" and "Masticatory Substances, Synthetic"

Useful natural elastomers include natural rubber such as smoked or liquid latex and guayule, natural gums such as jelutong, lechi caspi, perillo, sorva, massaranduba balata, massaranduba chocolate, nispero, rosidinha, chicle, gutta percha, gutta kataiu, niger gutta, tunu, chilte, chiquibul, gutta hang kang.

Useful synthetic elastomers include high molecular weight elastomers such as butadiene-styrene copolymers, polyisobutadiene and isobutylene-isoprene copolymers, low molecular weight elastomers such as polybutene, polybutadiene and polyisobutylene, vinyl polymeric elastomers such as polyvinyl acetate, polyethylene, vinyl copolymeric elastomers such as vinyl acetate/vinyl laurate, vinyl acetate/vinyl stearate, ethylene/vinyl acetate, polyvinyl alcohol or mixtures thereof.

Butadiene-styrene type elastomers, or SBR as they may be called, typically are copolymers of from about 20:80 to 60:40 styrene:butadiene monomers. The ratio of these monomers affects the elasticity of the SBR as evaluated by mooney viscosity. As the styrene:butadiene ratio decreases, the mooney viscosity decreases.

The structure of SBR typically consists of straight chain 1,3-butadiene copolymerized with phenylethylene (styrene) and provides the non-linear molecular nature of these elastomers. The average molecular weight of SBR is <600,000 g/mole.

Isobutylene-isoprene type elastomers, or butyl as they may be called, have molar percent levels of isoprene ranging from 0.2 to 4.0. Similar to SBR, as the isoprene:isobutylene ratio decreases, so does the elasticity, measured by mooney viscosity.

The structure of butyl rubber typically consists of branched 2-methyl-1,3-butadiene (isoprene) copolymerized with branched 2-methylpropene (isobutylene), and, as with SBR, this type of structure is non-linear in nature. The average molecular weight of SBR is in the range from 150,000 g/mole to 1,000,000 g/mole.

Polyisobutylene, or PIB as they may be called, type elastomers are polymers of 2-methylpropene and, as with SBR and butyl, are non-linear in nature. The low molecular weight elastomers provide soft chew characteristics to the polymer system and still provide the elastic qualities as do the other elastomers. Average molecular weights may range from about 30,000 to 120,000 g/mole and the penetration may range from about 4 millimeters to 20 millimeters. The higher the penetration, the softer the PIB. Similar to the SBR and butyl, the high molecular weight elastomers provide elasticity the gum. Average molecular weight may range from 120,000 to 1,000,000 g/mole. Again, if used at all, the molecular weight should be relatively low.

Function of Vinyl Polymers

The main components of the polymer system according to the invention is vinyl polymer(s).

Vinyl polymeric and copolymeric type elastomers provide tack resistance, vary the chew characteristics of the product made from these bases having vinyl polymers and offer hydrophilic properties beneficial to sensory perception of the final confectionery products.

For vinyl copolymeric types, the amount of vinyl laurate, vinyl stearate, or ethylene present in the vinyl laurate/vinyl acetate (VLNA), vinyl stearate/vinyl acetate (VSNA), or ethylene/vinyl acetate (EVA) copolymers respectively typically ranges from about 10 to about 60 percent by weight of the copolymer. Average molecular weights of these polymers may range from about 2,000 g/mole to about 100,000 g/mole.

The vinyl polymers as polyvinyl alcohol and polyvinyl acetate having an average molecular weight from about 8,000 g/mole to about 65,000 g/mole.

Function of Plasticizers

Elastomer plasticizers vary the firmness of the polymer system. Their specificity on polymer inter-molecular chain breaking (plasticizing) along with their varying softening points cause varying degrees of finished confectionery product firmness and compatibility when used in the polymer system.

Particular useful plasticizers according to the present invention are triacetin, acetylated mono- and di- and triglycerides of short chain fatty acids, acetylated mono- and di- and triglycerides of medium chain fatty acids, acetylated monoglycerides of long chain fatty acids, methyl ester of rosin, low molecular weight PVAc.

The plasticizers used may be of one type or of combinations of more than one type. Typically, the ratios of one to the other are dependent on each respective softening point, the effect on flavor release, and the respective degree of tack they cause to the gum.

Function of Waxes

Petroleum waxes aid in the curing of the finished confectionery product made from the polymer system as well as improve shelf-life and texture. Wax crystal size influence the release of flavor. Those waxes high in iso-alkanes have a smaller crystal size than those waxes high in normal-alkanes, especially those with normal-alkanes of carbon numbers less than 30. The smaller crystal size allows slower release of flavor since there is more hindrance of the flavor's escape from this wax versus a wax having larger crystal sizes. The compatability of polymer systems made using normal-alkanic waxes is less when compared to polymer systems made with iso-alkanic waxes.

List of Waxes

Petroleum wax (refined paraffin and microcrystalline wax) and paraffin wax is composed of mainly straight-chained normal-alkanes and branched iso-alkanes. The ratio of normal-alkanes to iso-alkanes varies.

The normal-alkanic waxes typically have carbon chain lengths >C-18 but the lengths are not predominantly longer than C-30. The branched and ring structures are located near the end of the chain for those waxes that are predominantly normal-alkanic. The viscosity of normal-alkanic waxes is <10 mm$^2$/s (at 100° C.) and the combined number average molecular weight is <600 g/mole.

The iso-alkanic waxes typically have carbon lengths that are predominantly greater than C-30. The branched chains and ring structures are located randomly along the carbon chain in those waxes that are predominantly iso-alkanic. The viscosity of iso-alkanic waxes is greater than 10 mm2/s (at 100° C.) and the combined number average molekylar weight is >600 g/mole.

Synthetic waxes are produced by means atypical of petroleum wax production and thus are not considered petroleum wax. The synthetic waxes may include waxes containing branched alkanes and copolymerized with monomers such as but not limited to propylene and polyethylene and Fischer Tropsch type waxes. Polyethylene wax is a synthetic wax containing alkane units of varying lengths having attached thereto ethylene monomers.

The natural waxes may include rice bran wax, bees' wax, carnauba wax or candelilla wax.

The waxes may be used alone or in any combination.

Function of Softeners

The selection of softeners has an influence on the softness of the base. Softeners modify the texture, cause the hydrophobic and hydrophilic components of the base to be miscible, and may further plasticize the synthetic polymers of the polymer system. The emulsifiers, which belong to the group of softeners, provide the polymer system with water-binding properties, which confer to the polymer system a pleasant smooth surface and reduce its adhesive properties.

Softeners suitable for use in the polymer system include triglycerides of non-hydrogenated, partially hydrogenated and fully hydrogenated vegetable oils and tallow, cocoa butter and degreased cocoa powder and in addition to these the emulsifiers.

The group of triglycerides include cottonseed, palm, palm kernel, coconut, safflower, rapeseed, sunflower, tallow, soybean, cocoa butter, medium chained triglycerides and the like.

The caproic, caprylic, capric, myristic, lauric and palmitic fatty acids of the triglycerides tend to plasticize the synthetic elastomers more than triglycerides containing predominantly stearic fatty acid.

To the group of emulsifiers belong the monoglycerides, diglycerides, acetylated mono and diglycerides, distilled mono- and diglycerides, glycerol monostearate, propylene glycol monostearate, Na-, K-, Mg- and Ca-stearates, glycerol triacetate, fatty acid monoglycerides (e.g. stearic, palmitic, oleic and linoleic acids), lactic acid esters and acetic acid esters of mono- and diglycerides, sugar esters of edible fatty acids also referred to as sucrose polyesters including those disclosed in WO 00/25598, lecithin and hydroxylated lecithin, most of these may contain triglyceride levels less than 2 percent by weight from their manufacturing processing, The softeners including the emulsifiers may be used alone or at least two or more in combination.

Function of Fillers

Generally, according to the invention, the amount of fillers should be kept low in the final confectionery product and preferably completely avoided in order to maintain the desired toffee-like textural properties, Fillers used in polymer system modify the texture of the polymer system and aid in processing. Particle size has an effect on cohesiveness, density and processing characteristics of the polymer system and its compounding. The smaller the particle size, the more dense and cohesive the final polymer system. Also, by selecting fillers based on their particle size distribution, initial mass compounding may be varied, thus allowing alteration of the compounding characteristics of the initial mass during polymer system processing and ultimately the final chew characteristics of gums made from these polymer systems.

Fillers suitable for use in the polymer system include magnesium and calcium carbonate, ground limestone and silicate types such as magnesium and aluminum silicate, kaolin and clay, aluminium oxide, silicium oxide, talc, as well as titanium oxide, mono-, di- and tricalcium phosphate, sodium sulphate, cellulose polymers such as ethyl, methyl and wood or mixtures thereof.

Talc filler may be used in the polymer system and confectionery product of the present invention that may come in contact with or employ acid flavors or provide an acidic environment needed to prevent degradation of an artificial sweetener by reacting with calcium carbonate type fillers. Mean particle size for calcium carbonate and talc fillers typically range from about 0.1 micron to about 15 microns.

The fillers may also include natural organic fibres such as fruit vegetable fibres, grain, rice, cellulose and combinations thereof.

Function and List of Other Optional Ingredients Such as Antioxidants, Colorants and Flavorants Antioxidants prolong shelf-life and storage of polymer system, finished confectionery product or their respective components including fats and flavor oils. Antioxidants suitable for use in polymer system include butylated hydroxyanisole (BHA), butylated hydroxytoluene (BHT), betacarotenes, tocopherols, acidulants such as Vitamin C, propyl gallate, other synthetic and natural types or mixtures thereof.

Flavorants and colorants impart characteristics or remove or mask undesired characteristics. Colorants may typically include FD&C type lakes, plant extracts, fruit and vegetable extracts and titanium dioxide flavorants may typically include cocoa powder, heat-modified amino acids and other vegetable extracts.

Preparation of Polymer Systems

Polymer systems are typically prepared by adding an amount of the high molecular weight PVAc, low molecular weight PVAc and plasticizer to a heated (10° C.-120° C.) sigma blade mixer with a front to rear speed ratio of from about 1.2:1 to about 2:1, the higher ratio typically being used for polymer system which requires more rigorous compounding of its medium/high molecular weight polymers.

The initial amounts of ingredients comprising the initial mass may be determined by the working capacity of the mixing kettle in order to attain a proper consistency and by the degree of compounding desired to break down the although slight amount of medium/high molecular weight polymers and increase chain branching. The longer the time of compounding, the use of lower molecular weight or softening point polymer system ingredients, the lower the viscosity and firmness of the final polymer system.

Compounding typically begins to be effective once the ingredients have massed together. Anywhere from 15 minutes to 90 minutes may be the length of compounding time Preferably, the time of compounding is from 20 minutes to about 60 minutes.

After the initial ingredients have massed homogeneously and compounded for the time desired, the balance of the polymer system ingredients are added in a sequential manner until a completely homogeneous molten mass is attained. Typically, any remainder of the polymer system components are added within 60 minutes after the initial compounding time.

Typical polymer system processing times may vary from about 0.5 to about 4 hours, preferably from about 0.5 to 1.5 hours, depending on the formulation. The final mass temperature when dumped may be between 70° C. and 130° C. and preferably between 100° C. and 120° C. The completed molten mass is emptied from the mixing: kettle into coated or lined pans, extruded or cast into any desirable shape and allowed to cool and solidify. Those skilled in the art will recognize that many variations of the above-described procedure may be followed.

Example 1

A polymer system according to an embodiment of the invention is prepared by a method corresponding to the method typically applied for gum base mixing. The applied method involved mixing in a Z-blade mixer. The polymer system comprises the following components:

95% by weight of low molecular weight PVAc (15000 g/mol Mw)

1% by weight of high molecular weight PVAc (60000 g/mol Mw)

4% triacetin.

It should be noted that extruding of the polymer system may advantageously be applied within the scope of the invention.

Example 2

A confectionery product is mixed on the basis of the polymer system of Example 1. The mixing is performed by a method corresponding to the method typically applied for mixing of gum base together with the hydrophilic chewing gum components. The confectionery product comprised:
- 0.3% by weight of high intensity sweetener
- 39% by weight of bulk sweetener (xylitol and sorbitol)
- 6% by weight of maltitol syrup
- 1.5% by weight of acid
- 3.2% by weight of lemon flavor
- 50% by weight of the polymer system of example 1

Confectionery products having the shape of an ellipsoid and having a weight of approximately 1.5 gram were formed of the resulting above-described mix.

The resulting confectionery product appeared as a chewing gum but the textural properties were comparable to the texture of toffee.

The release of sweetener and flavor were impressing and in good harmony with the toffee-like product.

Example 3

A confectionery product is mixed on the basis of the polymer system of Example 1. The mixing is performed by a method corresponding to method typically applied for mixing of gum base together with the hydrophilic chewing gum components. The confectionery product comprised:
- 0.4% by weight of high intensity sweetener
- 3% by weight of triacetin
- 43.6% by weight of bulk sweetener (xylitol and sorbitol)
- 6% by weight of maltitol syrup
- 7% by weight of liquorice flavor
- 40% by weight of the polymer system of example 1

Confectionery products having the shape of an ellipsoid and having a weight of approximately 1.5 gram were formed of the resulting above-described mix.

The resulting confectionery product appeared as a chewing gum but the textural properties were comparable to the texture of toffee.

The release of sweetener and flavor were impressing and in good harmony with the toffee-like product. It was furthermore observed that the confectionery product required a little more plasticizer compared to example 2. This is due to the fact that the lemon flavor and the associated acid tends to act as a significant supplementary plasticizer to the specifically applied triacetin.

Example 4

A confectionery product is mixed on the basis of the polymer system of Example 1. The mixing is performed by a method corresponding to method typically applied for mixing of gum base together with the hydrophilic chewing gum components. The confectionery product comprised:
- 0.4% by weight of high intensity sweetener
- 3% by weight of triacetin
- 47.6% by weight of bulk sweetener (xylitol and sorbitol)
- 6% by weight of maltitol syrup
- 3% by weight of chocolate/hazelnut flavor
- 40% by weight of the polymer system of example 1

Confectionery products having the shape of an ellipsoid and having a weight of approximately 1.5 gram were formed of the resulting above-described mix.

The resulting confectionery product appeared as a chewing gum but the textural properties were comparable to the texture of toffee.

The release of sweetener and flavor were impressing and in good harmony with the toffee-like product. Again, it was found advantageous to apply a little more plasticizer compared to example 2 for the same reasons as in example 3.

Example 5

A confectionery product is mixed on the basis of the polymer system of Example 1. The mixing is performed by a method corresponding to method typically applied for mixing of gum base together with the hydrophilic chewing gum components. The confectionery product comprised:
- 0.4% by weight of high intensity sweetener
- 3% by weight of triacetin
- 47.6% by weight of bulk sweetener (xylitol and sorbitol)
- 6% by weight of maltitol syrup
- 3% by weight of mint flavor
- 40% by weight of the polymer system of example 1

Confectionery products having the shape of an ellipsoid and having a weight of approximately 1.5 gram were formed of the resulting above-described mix.

The resulting confectionery product appeared as a chewing gum but the textural properties were comparable to the texture of toffee.

The release of sweetener and flavor were impressing and in good harmony with the toffee-like product. Again, it was found advantageous to apply a little more plasticizer compared to example 2 for the same reasons as in example 3.

Example 6

A confectionery product is mixed on the basis of the polymer system of Example 1. The mixing is performed by a method corresponding to method typically applied for mixing of gum base together with the hydrophilic chewing gum components. The confectionery product comprised:
- 59% by weight of sugar
- 6.3% by weight of glucose syrup
- 1.5% by weight of acid
- 3.2% by weight of lemon flavor
- 30% by weight of the polymer system of example 1

Confectionery products having the shape of an ellipsoid and having a weight of approximately 1.5 gram were formed of the resulting above-described mix.

The resulting confectionery product appeared as a chewing gum but the textural properties were comparable to the texture of toffee.

The release of sweetener and flavor were impressing and in good harmony with the toffee-like product.

Example 7

The confectionery products of example 2-6 were coated by a hard coating comprising xylitol.

Example 8

The confectionery products of example 4 and 5 were coated by a soft coating. The specifically applied soft coating is chocolate. It is noted that other soft coat materials may also be applied within the scope of the invention.

In an advantageous embodiment of the invention, chocolate may be applied as a coating, a product module or center filling as the polymer system has proved robust to such quite aggressive plasticizing component, which typically tends to dissolve conventional chewing gum formulations.

By evaluation it was noted that the desired toffee-character may be effectively supported and/or improved by the combination of toffee-like confectionery product according to the invention and chocolate.

Further layers of coatings may also be applied within the scope of the invention. It is noted that the confectionery product may be manufactured in several different ways within the scope of the invention, including well-known two processes or e.g. by extruding.

It is moreover noted that the shape, size and weight may vary significantly according to the current desired properties of the product.

Various shapes may thus e.g. include round, ellipsoid, square, multimodular, ring-formed, etc.

One particular interesting variant is a center-filled confectionery structure. The polymer system applied according to the invention has thus proved quite resistant to e.g. fat-based ingredients such as chocolate both prior to or subsequent to the chewing.

The invention claimed is:

1. Confectionery product comprising
a polymer system,
flavor and
sweetener,
wherein less than 10% by weight of said polymer system comprises polymer having a molecular weight (Mw) of greater than about 50000 g/mol,
wherein said confectionery product comprises at least one low molecular weight PVAc having a molecular weight (Mw) of about 2000 to 40000 g/mol in an amount of from about 70 to 99% by weight of the polymer system,
wherein said confectionery product comprises:
the polymer system in an amount of from about 5 to about 99% by weight,
flavor in an amount of about 0.001 to about 30% by weight and
sweeteners in an amount of about 5% to about 80% by weight selected from the group consisting of xylitol and sorbitol,
wherein said confectionary product is not center-filled,
wherein substantially the only water insoluble polymers present in the confectionary product are one or more polyvinyl acetates; and
wherein the confectionery product is substantially free of filler.

2. Confectionery product according to claim 1, wherein said confectionery product comprises a chewable tablet comprising a chewable polymer system.

3. Confectionery product according to claim 1, wherein said polymer system comprises plasticizers.

4. Confectionery product according to claim 1, wherein said polymer system comprises less than 30% by weight of plasticizers.

5. Confectionery product according to claim 1, wherein the confectionery product comprises less than 10% by weight of plasticizers.

6. Confectionery product according to claim 3, wherein said plasticizer comprises triacetin.

7. Confectionery product according to claim 3, wherein said plasticizer comprises acetylated glycerides.

8. Confectionery product according to claim 1, wherein said polymer system comprises less than 4% by weight of polymers having a molecular weight (Mw) of from about 50000 to 99999 g/mol.

9. Confectionery product according to claim 1, wherein said polymer system comprises less than 2% by weight of polymers having a molecular weight (Mw) of from about 100000 to 199999 g/mol.

10. Confectionery product according to claim 1, wherein said polymer system comprises less than 1% by weight of polymers having a molecular weight (Mw) of from about 200000 to 399999 g/mol.

11. Confectionery product according to claim 1, wherein said polymer system comprises less than 0.5% by weight of polymers having a molecular weight (Mw) of from about 399000 to 800000 g/mol.

12. Confectionery product according to claim 1, wherein the polymer system comprises:
at least one low molecular weight PVAc having a molecular weight (Mw) of about 2000 to 40000 g/mol,
at least one high molecular weight PVAc having a molecular weight (Mw) of 40001 to 200000 g/mol.

13. Confectionery product according to claim 1, wherein the polymer system comprises:
at least one low molecular weight PVAc having a molecular weight (Mw) of about 9000 to 30 000 g/mol.

14. Confectionery product according to claim 1 comprising at least one high molecular weight PVAc having a molecular weight (Mw) of 40000 to 100000 g/mol in an amount of from about 0.5 to 10% by weight of the polymer system.

15. Confectionery product according to claim 1, wherein said flavor comprises oil-based and/or hydrophilic flavors.

16. Confectionery product according to claim 1, wherein said confectionary product further comprises sugar.

17. Confectionery product according to claim 1, wherein said confectionery product is formed into a shape selected from the group consisting of cores, ellipsoid, balls, cylinders, squares, rectangular, hexagonal, strips, paraboloid, donut formed, ring formed, teddy bear formed and multi-modular.

18. Confectionery product according to claim 1, wherein the weight of the confectionery product is from about ¼ gram to about 10 grams.

19. Confectionery product according to claim 1, wherein the confectionery product comprises a coating.

20. Confectionery product according to claim 1, wherein the confectionery product comprises a pharmaceutically, cosmetically or biologically active substance.

21. Method of manufacturing a confectionery product comprises:
manufacturing a confectionery product by a batch process;
wherein the confectionery product comprises:
a polymer system,
flavor and
sweetener,
wherein less than 10% by weight of said polymer system comprises polymer having a molecular weight (Mw) of greater than about 50000 g/mol,
wherein said confectionery product comprises at least one low molecular weight PVAc having a molecular weight (Mw) of about 2000 to 40000 g/mol in an amount of from about 70 to 99% by weight of the polymer system,
wherein said confectionery product comprises:
the polymer system in an amount of from about 5 to about 99% by weight, flavor in an amount of about 0.001 to about 30% by weight and sweeteners in an amount of about 5% to about 80% by weight selected from the group consisting of xylitol and sorbitol, wherein the confectionary product is not center-filled, wherein substantially the only water insoluble polymers present in the confectionary product are one or more polyvinyl acetates, and wherein the confectionery product is substantially free of filler.

22. Method of manufacturing a confectionery product comprises:

manufacturing a confectionery product by an extruder process;

wherein the confectionery product comprises:

a polymer system, flavor and sweetener, wherein less than 10% by weight of said polymer system comprises polymer having a molecular weight (Mw) of greater than about 50000 g/mol, wherein said confectionery product comprises at least one low molecular weight PVAc having a molecular weight (Mw) of about 2000 to 40000 g/mol in an amount of from about 70 to 99% by weight of the polymer system, wherein said confectionery product comprises:

the polymer system in an amount of from about 5 to about 99% by weight, flavor in an amount of about 0.001 to about 30% by weight and sweeteners in an amount of about 5% to about 80% by weight selected from the group consisting of xylitol and sorbitol, wherein the confectionary product is not center-filled, wherein substantially the only water insoluble polymers present in the confectionary product are one or more polyvinyl acetates, and wherein the confectionery product is substantially free of filler.

23. Confectionary product according to claim 1, wherein said confectionary product comprises artificial sweeteners.

* * * * *